United States Patent [19]
Oakley et al.

[11] Patent Number: 5,236,959
[45] Date of Patent: Aug. 17, 1993

[54] PROCESS FOR RECYCLING POLYESTER/COTTON BLENDS

[75] Inventors: Etheridge O. Oakley, Matthews; Frederick J. Gorman, Charlotte, both of N.C.; James D. Mason, Alexandria, Va.

[73] Assignee: Hoechst Celanese Corporation, Somerville, N.J.

[21] Appl. No.: 851,035

[22] Filed: Mar. 12, 1992

[51] Int. Cl.$^5$ .................... C08J 11/04; C08J 11/24; D06M 11/38; D06M 13/00
[52] U.S. Cl. .................... 521/48.5; 524/41; 524/34; 8/115.51; 8/115.7; 8/116.1; 8/121
[58] Field of Search ............ 524/41, 34; 8/115.51, 8/115.7, 116.1, 121; 521/48.5

[56] References Cited

U.S. PATENT DOCUMENTS

| | | | |
|---|---|---|---|
| 2,729,618 | 1/1956 | Muller | 525/440 |
| 3,222,299 | 12/1965 | MacDowell | 521/48.5 |
| 3,257,335 | 6/1966 | Whitfield, Jr. et al. | 521/48.5 |
| 3,354,026 | 11/1967 | Illingworth | 8/141 |
| 3,488,298 | 1/1970 | Barkey et al. | 528/271 |
| 3,488,298 | 1/1970 | Barkey et al. | 562/485 |
| 3,703,488 | 11/1972 | Morton | 521/48.5 |
| 3,793,373 | 2/1974 | Grasemann et al. | 568/359 |
| 3,801,273 | 4/1974 | Mays | 8/141 |
| 3,830,759 | 8/1974 | Barkey | 521/48.5 |
| 3,843,321 | 10/1974 | Drelich | 8/141 |
| 3,907,868 | 9/1975 | Currie et al. | 560/98 |
| 3,937,671 | 2/1976 | Gruntfest et al. | 8/121 |
| 3,937,675 | 2/1976 | Gruntfest et al. | 521/48 |
| 3,960,485 | 6/1976 | Fantl et al. | 8/138 |
| 4,003,880 | 1/1977 | Sidebotham et al. | 528/487 |
| 4,092,105 | 5/1978 | Sullins | 8/81 |
| 4,092,481 | 5/1978 | Bunger | 560/77 |
| 4,118,187 | 10/1978 | Sidebotham et al. | 8/102 |
| 4,163,713 | 8/1979 | Keogh | 210/22 |
| 4,163,860 | 8/1979 | Delattre et al. | 560/96 |
| 4,345,039 | 8/1982 | Cowan et al. | 521/48 |
| 4,543,364 | 9/1985 | Nankee et al. | 528/497 |
| 4,609,680 | 9/1986 | Fujita et al. | 521/48 |

OTHER PUBLICATIONS

"Recovery of Fibers and Chemicals from Apparel Cutting Room Waste" by Jerry Goldbaugh of Georgia Tech Research Institute, Jul. 24, 1981—7 pages.

*Primary Examiner*—John Kight, III
*Assistant Examiner*—Jeffrey Culpeper Mullis
*Attorney, Agent, or Firm*—Philip P. McCann

[57] ABSTRACT

A process for recycling polyester/cotton blends by reducing the polyester to a lower dialkyl ester of terephthalic acid and reducing the cotton to cellulose acetate. The novel process to recycle the polyester/cotton blends includes the steps of (a) providing a blend of polyester and cotton fibers; (b) subjecting the polyester/cotton blend to a first alcoholysis in a bath containing an alcohol and an effective catalyst at a suitable temperature until the polyester is depolymerized to a lower molecular weight polyester oligomer; (c) remove the cotton fibers from the alcoholic solution of oligomers and process the recovered cotton fibers by pulping and acetylyzing processes to recover the cellulose acetate; and (d) alcoholyze the low molecular weight polyester oligomers to produce the lower dialkyl ester of terephthalic acid.

40 Claims, No Drawings

PROCESS FOR RECYCLING POLYESTER/COTTON BLENDS

FIELD OF THE INVENTION

The present invention relates to a process for recycling polyester/cotton blends to the components of lower dialkyl ester of terephthalic acid and cellulose acetate.

Millions of pounds of waste textiles consisting of various blends of polyester fibers and cellulose fibers such as cotton and the like are produced annually in the manufacture of cloth, clothing, and other textile products. Such textiles are generally treated with resinous and other materials of various types to impart special properties to the fabric such as crease resistance, flame retardency, and the like. Small quantities of this waste are collected by waste dealers for use in paper, inner linings, and a few other low value products. The remaining waste is either burned or buried in landfills. Disposal of such a large volume of solid waste is an increasing problem for the apparel industry. Implementation of the Resource Conservation and Recovery Act is expected to intensify the problem of such waste materials.

Waste polyester scrap can be recycled for reuse by various processes. Generally, such processes involved initially degrading the polyester with a lower alkyl alcohol, such as glycol, and subsequently recovering the dicarboxylic diester by crystallization and the alcohol from the resulting reaction mixture by distillation.

A process has been disclosed in U.S. Pat. No. 3,801,273 providing a method of recovering waste cellulose fibers from mixtures of waste cellulosic fibers, waste polyester and/or acrylic fibers and synthetic, cross-linked resinous material. The methods therein disclose heating a mixture of the waste cellulosic fibers, waste polyester and/or acrylic fibers and synthetic, cross-linked resin materials within the range of from 212° to 275° F. for a period of from ¾ to 5 hours in an aqueous treating solution containing an alkali metal hydroxide and one or more added, normally liquid chemical agents such as ketones, alcohols, lactones and sulfides which initiates the decomposition or solubilization of the waste polyester and/or acrylic fibers and synthetic, cross-linked resin materials; adding a neutral or alkaline oxidizing agent to the mixture of waste fibers and synthetic, cross-linked resin materials; heating the mixture of waste fibers in synthetic, cross-linked resin materials in the presence of the neutral or alkaline oxidizing agent to complete the decomposition or solublization of the waste polyester; and the recovery of the waste cellulosic fibers. A similar process is disclosed in U.S. Pat. No. 3,843,321. In the foregoing references, the cellulose fibers are washed and dried. Degradation of the cellulosic fibers is of such a low order that their usefulness in textile processes for the production of nonwoven fabrics is not impaired.

Various methods have been described in the prior art for the recovery of polyester from cellulose fibers. U.S. Pat. No. 3,937,671 discloses a process in which textile waste composed of blended polyester and cellulose fibers are subjected to the action of glacial acetic acid and acetic anhydride in the presence of a catalyst under conditions which serve to convert the cellulose component of the waste to cellulose acetate which is separated from the unreacted polyester component in the form of a solution adapted to be used in the manufacture of cellulose derivatives where the polyester is removed in a form which may be garnetted to obtain a staple fiber for reuse.

A similar process has been disclosed in U.S. Pat. No. 3,937,675. In the disclosed process, textile waste formed of blended cellulose and polyester fibers are treated with a mineral acid agent such as sulfuric acid, under conditions which serve to hydrolyze the cellulose and convert it to a form which is readily removed from the polyester fibers while leaving the polyester fibers substantially unaffected. The cellulose material is recovered in the form of fibrets adapted for use as such or for treatment in producing other cellulosic compounds whereas the polyester fiber recovered may be garnetted for reuse in either spun yarn manufacture or in nonwoven processes.

In such processes, the cotton is recovered in a highly crystalline form of hydrocellulose with a degree of polymerization determined by viscosity measurements of approximately 100. Dimensionally, the fibrets range in length from several microns to several millimeters and they have the typical diameters of cotton fibers. On the other hand, the polyester material separated from the cotton was washed with water and was dried and was then garnetted with the result that essentially undamaged polyester fibers adapted for reuse in spun yarn manufacture or in nonwoven processes were recovered.

These methods are very expensive and have not met with commercial success. Large quantities of reactants per weight of waste material are needed in the process of the U.S. Pat. No. 3,937,671 and the recovery materials must be dried. High reaction temperatures and large quantities of acid are necessary in the process of U.S. Pat. No. 3,937,675 and again the recovered materials must be dried.

Accordingly, there is a need for an economical process for recovering polyester fibers and cellulosic materials in useful forms from polyester/cotton textile waste.

It is another object of this invention to recover polyester fibers and cellulosic materials in useful forms from such textile waste. It is still another object of this invention to provide a process for recycling polyester/cotton blends which does not include a preliminary aqueous acid treatment. These and other objects of the invention will be apparent to one skilled in the art as the description thereof proceeds.

SUMMARY OF THE INVENTION

The present invention provides a process which is effective and economical in recycling polyester/cotton blend by reducing the polyester to a lower dialkyl ester of terephthalic acid and reducing the cotton to cellulose acetate. In particular, the present invention discloses a process for converting polyester and cotton blends to a lower dialkyl ester of terephthalic acid and cellulose acetate, including the steps of: (a) providing a blend of polyester and cotton fibers; (b) subjecting the blend to a first alcoholysis in a bath containing an alcohol and an effective catalyst and having a suitable temperature until the polyester is depolymerized; (c) removing the remaining cotton portion from the alcoholic solution of oligomers generated during the first alcoholysis; (d) performing a second alcoholysis of the depolymerized polyester in a bath containing a lower alkyl alcohol in the presence of an effective catalyst to produce the lower dialkyl ester of terephthalic acid; and (e) processing the recovered cotton fibers through pulping and acetylyzing processes until the cellulose acetate is recovered.

DESCRIPTION OF THE PREFERRED EMBODIMENTS

In accordance with the present invention, sources for polyester/cotton blends may be obtained from various sources including, but not limited to, cut and sew waste from manufacturers, spinning waste from manufacturers and post consumer garments. It is noted that foreign materials should be removed from such sources, including other polymers such as nylon, and metallic objects such as zippers and buttons. It is also preferred that the polyester contained in the scrap materials be 100 percent PET, although up to 10 percent copolymer such as isophthalic acid may be still used, but will affect the yield of the diester of terephthalic acid produced. It is also noted that the cotton material used in the scrap should not be mercerized. This is a common process used in the cotton industry to improve the luster of the cotton material.

Once the scrap material has been accumulated, it is preferred that the scrap material be cut and chopped into small pieces for ease of handling and subsequent transfer into a reaction vessel. One example would be one inch squares of fabric. The material is then treated by a first alcoholysis in a normal reaction vessel. In such vessels, the scrap polyester/cotton blend is deposited, along with a lower alkyl alcohol and a suitable catalyst. Such alcohols used may include ethylene glycol, butane diol, propane diol, and methanol. Preferably, ethylene glycol is used. Suitable mono or di alcohols are suitable for use in the present invention. It is noted at this time that if methanol is used, then the DMT may be prepared directly.

Suitable catalysts which may be used would include basic alkali metal salts, such as sodium carbonate, lithium carbonate, sodium hydroxide or lithium hydroxide. Quantities of the alcohol and the catalyst used would be based on the amount of the polyester/cotton blend used in the reaction vessel. Preferably, the weight of alcohol used should be about three to four times the weight of the polyester/cotton blend sample. For example, if 100 grams of polyester/cotton blend is put into the polymerization vessel, then 300 to 400 grams of an alcohol, such as ethylene glycol is used. The amount of the catalyst used should be about 0.25 percent of the polyester/cotton blend weight.

The first alcoholysis is preferably run at atmospheric pressure with a constant nitrogen purge. It is noted that when methanol is used, the reaction is run at between 150 and 250 psig. As the reaction is started, the temperature will increase as the reaction proceeds, but should run between 180° C. to 210° C. for four to six hours. This reaction time can be shortened by using a monomer heel in the reaction vessel. The first alcoholysis is run until a degree of polymerization of less than 15 is obtained and preferably a degree of polymerization of less than 3. The reaction product is cooled to 150° C. to 170° C. The resultant slurry is then filtered to separate the cotton from the polyester slurry.

The means for removing the cotton from the reaction products includes filtering, centrifuging or belt presses. Preferably, in the present embodiment, filtering is used. The filtering may be either gravity or a vacuum type filter or a pressure filter. Typical filter media include glass frits for laboratory purposes, and stainless packing for production purposes. Subsequent to the filtering, the cotton can be air dried or nitrogen dried and washed with methanol to remove any residual oligomers and contaminants from the cotton.

Subsequent to the filtering, two processes will be done on the polyester oligomers and cotton. The polyester oligomers will process through a second alcoholysis from which a lower dialkyl ester of terephthalic acid will be produced. Generally, the alcohol used is an alcohol having an alkyl of less than 6 carbons and typically 1 or 2 carbons, and preferably methanol is used. A catalyst such as sodium carbonate is added and pressure in the range of 0 to 50 psi is applied to the alcoholysis at a temperature from 65° C. to 100° C. depending on the degree of polymerization of the oligomer. The process is continued until the diester of terephthalic acid is produced.

The cotton produced from the washing may be processed to cellulose acetate. The process for this includes both pulping the cotton and acetylation of the product. For laboratory pulping, the caustic digestion of the cotton is processed at 130° C., 4 percent on cellulose, 10 percent consistency for 1 hour subsequent to the caustic digestion, the product is hypochlorite bleached at 60° C., 3 percent solution, 10 percent consistency for 1.3 hours. Subsequently, the product is treated with cold caustic extraction at 40° C., 9.5 percent solution, 6 percent consistency for 30 minutes. The product is then washed. The cotton product is then acetylated to produce the triacetate cellulose.

EXAMPLES

To the bottom of a 1 L 2-piece reaction vessel with 3-24/40 ground glass joints was added 160 g of 50/50 polyester/cotton blend fabric (or any form of blend), 32 g of BHET made from glycolysis of PET bottle flake, 600 g of fresh EG, and 0.5 g of $Na_2CO_3$ as catalyst. The top of the vessel was then put in place and equipped with a reflux column and condenser with nitrogen inlet, and two glass stoppers. The vessel and contents were purged with nitrogen for 45 min prior to the application of heat. The reaction was then heated at reflux (approximately 195°-200° C.) for 5 hours. The resulting mixture was allowed to cool to about 160° C. and was suction filtered through a pre-heated 2 L fritted filter. 514 g of EG solution was recovered with the remainder of the solution being soaked up by the residual cotton. The cotton was washed on the filter with 500 g of fresh EG. The recovered EG solution was saved and combined with the previous EG solution for concentration on the rotary evaporator. The cotton was further washed on the filter with 2×420 g of fresh methanol. These washings were combined and used as the solvent/reactant in the methanolysis step below. The cotton was then suction dried on the filter with application of a rubber dam over the top of the funnel allowing for more effective vacuum buildup and allowed to air dry for 24 hours at which time the still slightly wet cotton weight was 100 g.

The EG solutions (approx. 725 ml total) were concentrated by rotary evaporator to ⅓ of its original volume giving a solution with approximate concentration of BHET of 2 mol/L. This was used in the methanolysis reaction below.

To a 2 L 3-neck round bottom flask equipped with an air condenser and water condenser in sequence, and glass stoppers was added the combined methanol washes from above, and 0.5 g $Na_2CO_3$ as catalyst. The solution was heated to approximately 40° C. at which time the concentrated (and still hot) EG/BHET solution was added. The reaction was allowed to reflux for about 30 minutes and allowed to cool. The resulting DMT was suction filtered, washed with a small amount of cold methanol and air dried. The resulting yield of DMT was 90 g (85% of theoretical). Analysis of the DMT showed it to be pure by thin layer chromatography (>98% purity).

Thus, it is apparent that there has been provided in accordance with the invention a method of recycling polyester/cotton blends to recover lower dialkyl esters of terephthalic acid and cellulose acetate. While the invention has been described in conjunction with the specific embodiments thereof, it is evident that many alternatives, modifications and variations will be apparent to those skilled in the art in light of the foregoing description. Accordingly, it is intended to embrace all such alternatives, modifications that fall within this sphere and scope of the invention.

That which is claimed is:

1. A process for converting polyester and cotton blends to a lower dialkyl ester of terephthalic acid and cellulose acetate comprising the steps of:
   providing a blend of polyester fibers and cotton fibers;
   alcoholizing said blend in a bath containing a lower alkyl alcohol processing one or two alcohol groups and an effective catalyst and having a suitable temperature until the polyester is depolymerized to a diester of terephthalic acid;
   removing the cotton fibers from the bath and processing the cotton fibers through pulping and acetylyzing processes until the cellulose acetate is produced; and
   alcoholizing the diester of terephthalic acid in the presence of a lower alkyl alcohol processing one alcohol group and an effective catalyst to produce the lower dialkyl ester of terephthalic acid.

2. The process according to claim 1 wherein said lower dialkyl ester of terephthalic acid is dimethylterephthalate.

3. The process according to claim 1 wherein the lower alkyl alcohol processing one or two alcohol groups is ethylene glycol.

4. The process according to claim 1 wherein the catalyst for alcoholysis is selected from the group consisting of sodium carbonate, sodium methoxide and sodium hydroxide.

5. A process for converting polyester and cotton blends to a lower dialkyl ester of terephthalic acid and cellulose acetate comprising the steps of:
   providing a blend of polyester fibers and cotton fibers;
   glycolyzing said blend in a bath containing ethylene glycol and an effective catalyst and having a temperature ranging from about 150° C. to about 225° C. until the polyester is depolymerized to low molecular weight polyester oligomers;
   removing the cotton fibers from the bath and processing the cotton fibers through pulping and acetylyzing processes until cellulose acetate is produced; and
   alcoholizing the diester of terephthalic acid in the presence of a lower alkyl alcohol processing one alcohol group and an effective catalyst to produce the lower dialkyl ester of terephthalic acid.

6. The process according to claim 5 wherein said lower dialkyl ester of terephthalic acid is dimethylterephthalate.

7. The process according to claim 5 wherein the catalyst for alcoholysis is selected from the group consisting of sodium carbonate, sodium methoxide and sodium hydroxide.

8. A process for converting polyester and cotton blends to a lower dialkyl ester of terephthalic acid and cellulose acetate comprising the steps of:
   providing a polyester fiber and a cotton fiber;
   alcoholizing of said blend in a bath containing a lower alkyl alcohol processing one or two alcohol groups and an effective catalyst and having a temperature ranging from about 150° C. to about 225° C. until the polyester is depolymerized to a diester of terephthalic acid;
   removing the cotton fibers from the bath and processing the cotton fibers through pulping and acetylyzing processes until the cellulose acetate is produced;
   removing the alcohol from the diester of terephthalic acid solution to achieve a solution having a diester of terephthalic acid concentration of greater than 0.75 moles/liter; and
   alcoholizing the diester of terephthalic acid in the presence of a lower alkyl alcohol possessing one alcohol group and an effective catalyst to produce the lower dialkyl ester of terephthalic acid.

9. The process according to claim 8 wherein said lower dialkyl ester of terephthalic acid is dimethylterephthalate.

10. The process according to claim 8 wherein the lower alkyl alcohol processing one or two alcohol groups is ethylene glycol.

11. The process according to claim 8 wherein the catalyst for alcoholysis is selected from the group consisting of sodium carbonate, sodium methoxide and sodium hydroxide.

12. A process for converting polyester and cotton blends to a lower dialkyl ester of terephthalic acid and cellulose acetate comprising the steps of:
   providing a blend of polyester fibers and cotton fibers;
   alcoholizing said blend in a bath containing a lower alkyl alcohol processing one or two alcohol groups and an effective catalyst and having a temperature ranging from about 150° C. to about 225° C. until the polyester is depolymerized to low molecular weight polyester oligomers with a degree of polymerization ranging from about 1 to 15;
   separating and removing the remaining cotton portion from the alcoholic solution of said oligomers generated during said first alcoholysis;
   rinsing of said cotton with a lower alkyl alcohol processing one or two alcohol groups to remove residual polyester oligomers from the cotton surface;
   processing the cotton fibers through pulping and acetylyzing processes until the cellulose acetate is produced;
   alcoholizing said low molecular weight polyester oligomers in a bath containing a lower alkyl alcohol possessing one alcohol group in the presence of an effective catalyst to produce the lower dialkyl ester of terephthalic acid.

13. The process according to claim 12 wherein said lower dialkyl ester of terephthalic acid is dimethyl terephthalate.

14. The process according to claim 12 wherein the lower alkyl alcohol processing one or two alcohol groups in the first alcoholysis is ethylene glycol.

15. The process according to claim 12 wherein the catalyst for said first alcoholysis is a hydroxide salt of an alkali metal.

16. The process according to claim 12 wherein the catalyst for said first alcoholysis is a methoxide salt of an alkali metal.

17. The process according to claim 12 wherein the catalyst for said first alcoholysis is a carbonate salt of an alkali metal.

18. The process according to claim 12 wherein the catalyst for said second alcoholysis is a hydroxide salt of an alkali metal.

19. The process according to claim 12 wherein the catalyst for said second alcoholysis is a methoxide salt of an alkali metal.

20. The process according to claim 12 wherein the catalyst for said second alcoholysis is a carbonate salt of an alkali metal.

21. The process according to claim 12 wherein said lower alkyl alcohol processing one alcohol group is methanol.

22. A process for converting polyester and cotton blends to a lower dialkyl ester of terephthalic acid and cellulose acetate comprising the steps of:
    providing a blend of polyester fibers and cotton fibers;
    a first alcoholysis of said blend in a bath containing a lower alkyl alcohol possessing one or two alcohol groups and an effective catalyst and having a temperature ranging from about 150° C. to about 225° C. until the polyester is depolymerized to low molecular weight polyester oligomers with a degree of polymerization ranging from about 1 to 15;
    separating and removing the remaining cotton portion from the alcoholic solution of said oligomers generated during said first alcoholysis;
    rinsing of said cotton with a lower alkyl alcohol possessing one or two alcohol groups to remove residual polyester oligomers from the cotton surface;
    processing the cotton fibers through pulping and acetylyzing processes until the cellulose acetate is produced;
    concentrating the solution of said low molecular weight polyester oligomers to achieve a polyester oligomer concentration of greater than 0.75 moles/liter; and
    alcoholizing said concentrated solution of low molecular weight polyester oligomers in a bath containing a lower alkyl alcohol possessing one alcohol group and in the presence of an effective catalyst at a temperature range of about 60° C. to 70° C. to produce the lower dialkyl ester of terephthalic acid.

23. The process according to claim 22 wherein said lower dialkyl ester of terephthalic acid is dimethyl terephthalate.

24. The process according to claim 22 wherein said lower alkyl alcohol possessing one or two alcohol groups in the first alcoholysis is ethylene glycol.

25. The process according to claim 22 wherein the catalyst for said first alcoholysis is a hydroxide salt of an alkali metal.

26. The process according to claim 22 wherein the catalyst for said first alcoholysis is a methoxide salt of an alkali metal.

27. The process according to claim 22 wherein the catalyst for said first alcoholysis is a carbonate salt of an alkali metal.

28. The process according to claim 22 wherein the catalyst for said second alcoholysis is a hydroxide salt of an alkali metal.

29. The process according to claim 22 wherein the catalyst for said second alcoholysis is a methoxide salt of an alkali metal.

30. The process according to claim 22 wherein the catalyst for said second alcoholysis is a carbonate salt of an alkali metal.

31. The process according to claim 22 wherein said means of concentrating polyester oligomers is distillation at a temperature of between 190° C. and 210° C.

32. The process according to claim 22 wherein said means of concentrating polyester oligomers is vacuum distillation at a temperature of between 100° C. and 200° C. at a pressure of less than or equal to 100 mm Hg absolute.

33. The process according to claim 22 wherein said means of concentrating polyester oligomers is successive repetition of said first alcoholysis using a new amount of polyester/cotton blend article and the alcoholic polyester oligomer solution as the source of said lower alkyl alcohol possessing one or two alcohol groups.

34. The process according to claim 22 wherein said lower alkyl alcohol possessing one alcohol group is methanol.

35. A process for converting polyester and cotton blends to a regenerated polyester and cellulose acetate comprising the steps of:
    providing a blend of polyester fibers and cotton fibers;
    alcoholysis of said blend in a bath containing a lower alkyl alcohol possessing one or two alcohol groups and an effective catalyst and having a temperature ranging from about 150° C. to 225° C. until the polyester is depolymerized to low molecular weight polyester oligomers with a degree of polymerization ranging from about 1 to 15;
    separating and removing the remaining cotton portion from the alcoholic solution of said oligomers generated during said first alcoholysis;
    rinsing of said cotton with a lower alkyl alcohol possessing one or two alcohol groups to remove residual polyester oligomers from the cotton surface;
    processing the cotton fibers through pulping and acetylyzing processes until the cellulose acetate is produced;
    polymerizing of said low molecular weight polyester oligomers using an effective polymerization catalyst at a temperature range of about 220° C. and 300° C. and a pressure of less than 5 mm Hg absolute to obtain a regenerated polyester.

36. The process according to claim 35 wherein the lower alkyl alcohol possessing one or two alcohol groups in the first alcoholysis is ethylene glycol.

37. The process according to claim 35 wherein the catalyst for said alcoholysis is a hydroxide salt of an alkali metal.

38. The process according to claim 35 wherein the catalyst for said alcoholysis is a methoxide salt of an alkali metal.

39. The process according to claim 35 wherein the catalyst for said alcoholysis is a carbonate salt of an alkali metal.

40. The process according to claim 35 wherein said polymerization catalyst is selected from the group consisting of antimony (III) oxide, germanium (IV) oxide, lower alkyl titanates, stannoic acid and its esters, and antimony (III) glycolate, at a level of from about 15 ppm based on the metal portion of the catalyst to about 350 ppm based on the metal portion of the catalyst.

* * * * *